(12) United States Patent
Zhou

(10) Patent No.: US 10,349,828 B2
(45) Date of Patent: Jul. 16, 2019

(54) PORTABLE WAVEFRONT ABERROMETER

(71) Applicant: Smart Vision Labs, Inc., New York, NY (US)

(72) Inventor: Yaopeng Zhou, New York, NY (US)

(73) Assignee: Smart Vision Labs, Inc., New York, NY (US)

( * ) Notice: Subject to any disclaimer, the term of this patent is extended or adjusted under 35 U.S.C. 154(b) by 20 days.

(21) Appl. No.: 15/687,107

(22) Filed: Aug. 25, 2017

(65) Prior Publication Data

US 2017/0347876 A1    Dec. 7, 2017

Related U.S. Application Data

(63) Continuation of application No. 14/628,325, filed on Feb. 23, 2015, now Pat. No. 9,801,538, which is a continuation of application No. 14/247,784, filed on Apr. 8, 2014, now Pat. No. 9,066,683.

(60) Provisional application No. 61/922,337, filed on Dec. 31, 2013, provisional application No. 61/809,925, filed on Apr. 9, 2013.

(51) Int. Cl.
| | |
|---|---|
| *A61B 3/10* | (2006.01) |
| *A61B 3/00* | (2006.01) |
| *A61B 3/14* | (2006.01) |
| *A61B 3/18* | (2006.01) |

(52) U.S. Cl.
CPC .......... *A61B 3/1015* (2013.01); *A61B 3/0008* (2013.01); *A61B 3/10* (2013.01); *A61B 3/14* (2013.01); *A61B 3/185* (2013.01)

(58) Field of Classification Search
CPC ..... A61B 3/1015; A61B 3/185; A61B 3/0008; A61B 3/10; A61B 3/14
See application file for complete search history.

(56) References Cited

U.S. PATENT DOCUMENTS

| | | |
|---|---|---|
| 6,264,328 B1 | 6/2001 | Williams et al. |
| 9,066,683 B2 | 6/2015 | Zhou |
| 2003/0142271 A1 | 7/2003 | Ross et al. |
| 2004/0189942 A1 | 9/2004 | Yoon |
| 2011/0299036 A1 | 12/2011 | Goldenholz |

FOREIGN PATENT DOCUMENTS

| | | |
|---|---|---|
| EP | 1882444 A1 | 1/2008 |
| JP | 2008093118 | 4/2008 |
| WO | 2004017825 A1 | 3/2004 |

(Continued)

OTHER PUBLICATIONS

International Search Report and Written Opinion dated Jan. 30, 2015 for PCT/US2014/059363, 16 pages.

(Continued)

*Primary Examiner* — Jack Dinh
(74) *Attorney, Agent, or Firm* — Lowenstein Sandler LLP

(57) ABSTRACT

Systems and methods for measuring an aberration of a patient's eye are disclosed. In one embodiment, a portable wavefront aberrometer comprises a housing having a proximal end and a distal end, wherein an aperture is formed in the housing at the proximal end; an activatable light source; a light detector; and optical components housed within the housing, the optical components comprising a microlens array, a plurality of lenses, one or more reflectors, and one or more beam splitters, wherein the optical components are arranged to define a first light path and a second light path.

9 Claims, 7 Drawing Sheets

(56) References Cited

FOREIGN PATENT DOCUMENTS

WO   2012177544 A1   12/2012
WO   2015003062 A1   1/2015

OTHER PUBLICATIONS

International Search Report and Written Opinion dated Jun. 27, 2016 for PCT/US2016/012678, 15 pages.
Porter, et al., "Adaptive Optics for Vision Science: Principles, Practices, Design, and Applications", pp. 155-187, Oct. 20, 2005, 33 pages.

PORTABLE WAVEFRONT ABERROMETER

CROSS REFERENCE TO RELATED APPLICATIONS

This application is a continuation of U.S. Non-Provisional patent application Ser. No. 14/628,325, filed Feb. 23, 2015, which is a continuation of U.S. Non-Provisional patent application Ser. No. 14/247,784, filed Apr. 8, 2014, which claims the benefit of priority of both U.S. Provisional Patent Application No. 61/922,337, filed Dec. 31, 2013, and U.S. Provisional Patent Application No. 61/809,925, filed Apr. 9, 2013, the disclosures of which are hereby incorporated by reference herein in their entireties.

TECHNICAL FIELD

Implementations of the present disclosure relate to optical devices for detecting and measuring refractive errors of a patient's eye.

BACKGROUND

In the United States, vision tests are not routinely provided to children under the age of 6, with only 14% of children under the age of 6 having had a vision exam. In addition, over 500 million people worldwide suffer from refractive error-related illness, with more than 90% of these people being in developing countries. Such conditions are likely to worsen over time if not identified and corrected early.

Several factors may prohibit both early detection and detection in general. One is communication, as may be the case with a small child who cannot clearly indicate that he/she is experiencing an ailment or in a developing country in which a patient may not be able to communicate effectively with a care provider. Another factor is cost, which may be particularly limiting in developing countries as equipment for detecting refractive errors can be expensive and well-trained personnel for operating the equipment and analyzing the results may be inaccessible or have limited availability.

BRIEF DESCRIPTION OF THE DRAWINGS

The present disclosure is illustrated by way of example, and not by way of limitation, in the figures of the accompanying drawings in which like references indicate similar elements. It should be noted that different references to "an" or "one" implementation in this disclosure are not necessarily to the same implementation, and such references mean at least one.

DETAILED DESCRIPTION

Figure 1:
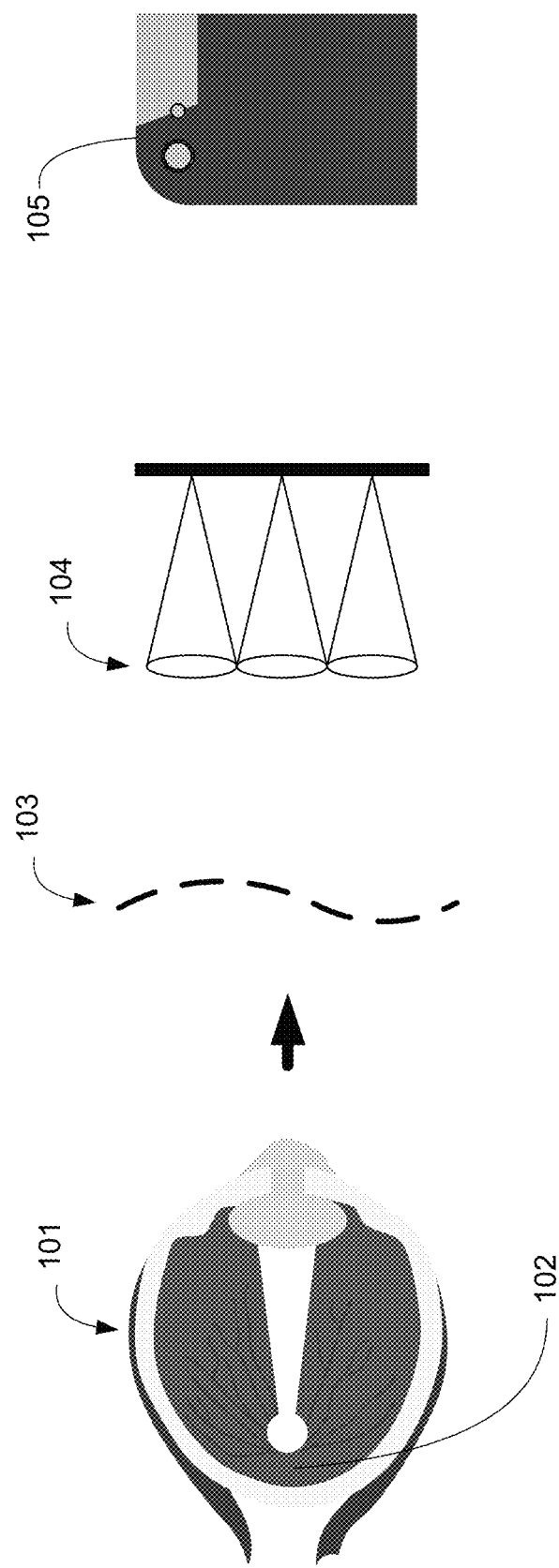
FIG. 1 depicts an eye, a wavefront generated by light reflected from the eye's retina, and an array of lenses that focus this light onto a light detector of a mobile device camera.

The subject matter of this application relates to diagnostic equipment used most typically by ophthalmologists and optometrists to detect and measure refractive errors of a patient's eye. More particularly, the subject matter of this application pertains to modules that are capable of being reversibly attached to a portable computing device, such as a smartphone, thereby creating a functional wavefront aberrometer. The subject matter of this application utilizes a light source, such as a laser present on the module, to generate the light to be reflected from the eye. Further, the disclosed device utilizes the portable computing device's camera to capture this reflected light, which can then be transformed by software on the portable computing device and provided for use by medical professionals and others.

One objective of the subject matter of this application is to provide a module that, when reversibly coupled to a portable computing device such as a smartphone, creates a functional wavefront aberrometer. A further objective is to provide a lower-cost wavefront aberrometer by utilizing a portable computing device likely to already be owned by a consumer. Another objective is to provide a lower-cost wavefront aberrometer module that could be branded by an optical professional and lent to a patient for use to provide the optical professional with multiple data sets tracking changes in the refractive error of the patient's eyes. Yet another objective is to provide a lower-cost wavefront aberrometer module that could be branded by an optical professional and lent to a patient to allow that patient to obtain refractive measurements without a visit to the optical professional, and optionally, to have those measurements transmitted to the optical professional for diagnostic or screening purposes, or to fashion or otherwise make ready corrective lenses for purchase. The nature of the implementations disclosed herein may reduce the cost associated with a wavefront aberrometer, making it a feasible device for home use or in areas of limited medical infrastructure, such as developing countries.

These objectives can be obtained by a wavefront aberrometer module (the "module") that can be reversibly attached to a mobile computing device (the "mobile device"), such as a smartphone, personal digital assistant, laptop or palmtop computer. Smartphones are mobile phones having a computer, an illuminated screen, and a camera, among other features. Other mobile devices having a camera may be used in accordance with the subject matter of this application. For example, a mobile devices that may be used in accordance with the disclosed implementations could be a phone (or smartphone) equipped with a camera, although other devices such as tablet computers, laptop computers, certain audio or video players, and ebook readers may also be used, which all may include a light detector (e.g., a camera) and either a central processing unit or a transceiver for communicating the information captured by the camera to another device with a central processing unit. The module may include a guide for positioning or attaching the module to the mobile device to provide a beam path whereby light from the light source can be directed towards the patient's eye, and provide a beam path whereby light from the light source that is reflected off the patient's eye travels through an array of microlenses and then onto the light detector.

The subject matter of this application separates certain components of a wavefront aberrrometer into two components that may be joined to form a functioning unit. One component, the module, includes a system of focusing and directing light to a patient's eye, and a system of directing light reflected from the patient's eye, through an array of lenses, and finally to a light detector which includes a portion of the mobile device. This separation allows a primary benefit of the subject matter of this application, which is the division of cost and complexity of a wavefront aberrometer into a module portion and a mobile device portion, said mobile device portion being already likely owned or available to a consumer.

In use, the module may be reversibly attached to the mobile device and held in position so that the light beam from the module's light source is focused by the module onto the wearer's eye. When in position, the module's light source is activated causing this light to bounce off the wearer's retina and pass through the microlens array before ultimately being detected by the mobile device's camera. The data gathered by the camera may then be processed through algorithms known in the art by the mobile device's microcomputer, or the data may be transmitted by the mobile device to a different computer for processing. The data may be presented to the end user in an unprocessed form, or it may be presented in a post-processing format, such as an eyeglasses prescription or a Snellen fraction. Software on the mobile device may also limit the information presented to the end user and send either the unprocessed or processed data to the optical professional for diagnostic use and/or to prepare corrective lenses.

The following description and drawings referenced herein illustrate an implementation of the application's subject matter, and are not intended to limit the scope. Those of ordinary skill in the art will recognize that other implementations of the disclosed method are possible. All such implementations should be considered within the scope of the claims. Each reference number consists of three digits. The first digit corresponds to the figure number in which that reference number is first shown. Reference numbers are not necessarily discussed in the order of their appearance in the figures.

FIG. 1 depicts a simple overview of an aspect of an implementation in which light, as represented by a light wavefront (103), is reflected off a retina (102) of a patient's eye (101). This light (103) is separated by a microlens array (104) into an array of light spots and focused by the microlens array onto a two-dimensional light detector (105). As shown in this illustration, the two-dimensional light detector may be the camera of a mobile device, such as a smart phone. It should be understood that the combination of the module with a smartphone in this implementation should not limit the claims to the use of a smartphone, as any mobile device can be used with a module as disclosed in this application.

Figure 2:
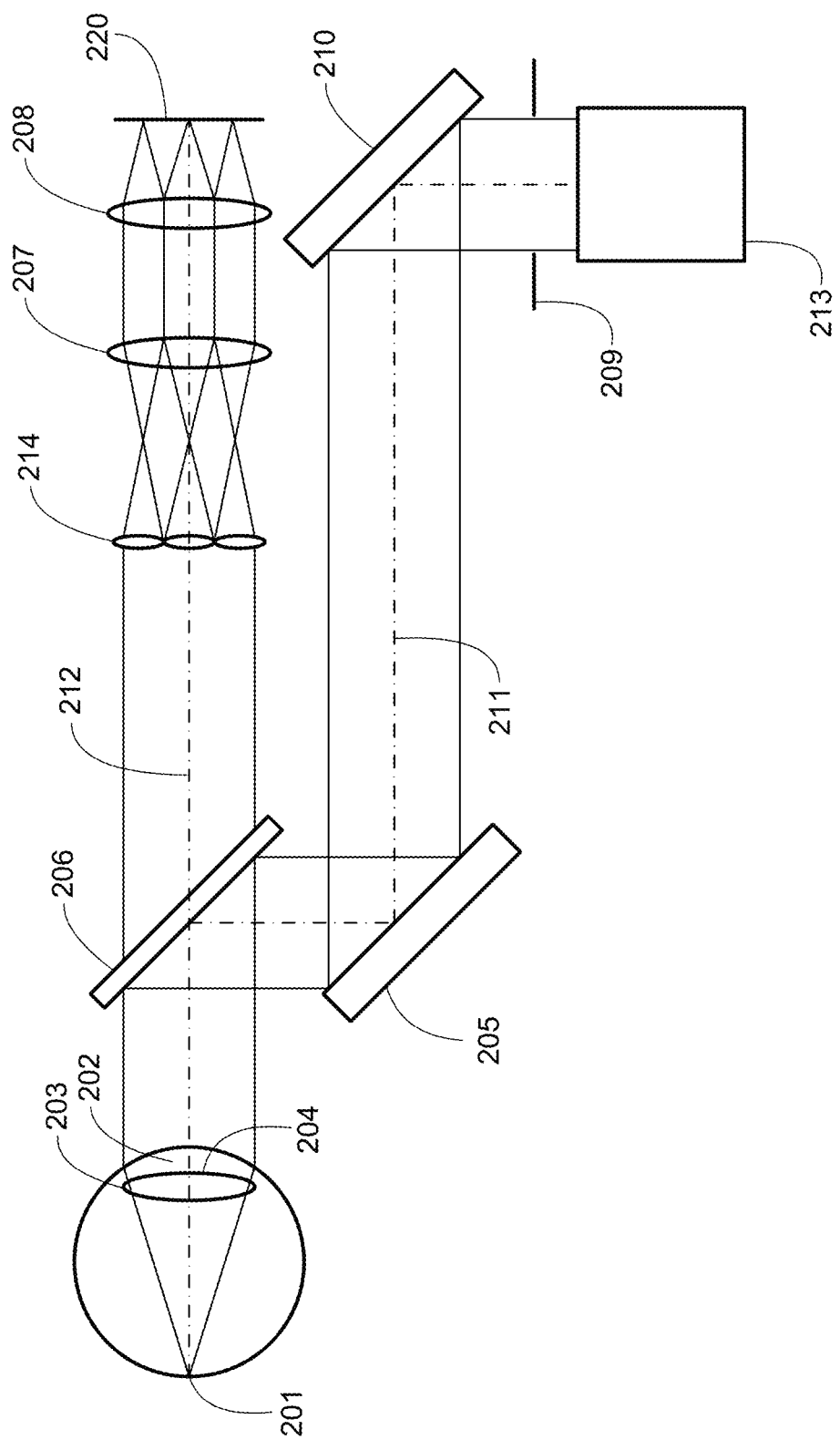
FIG. 2 illustrates a design of the disclosed wavefront aberrometer.
Figure 3:
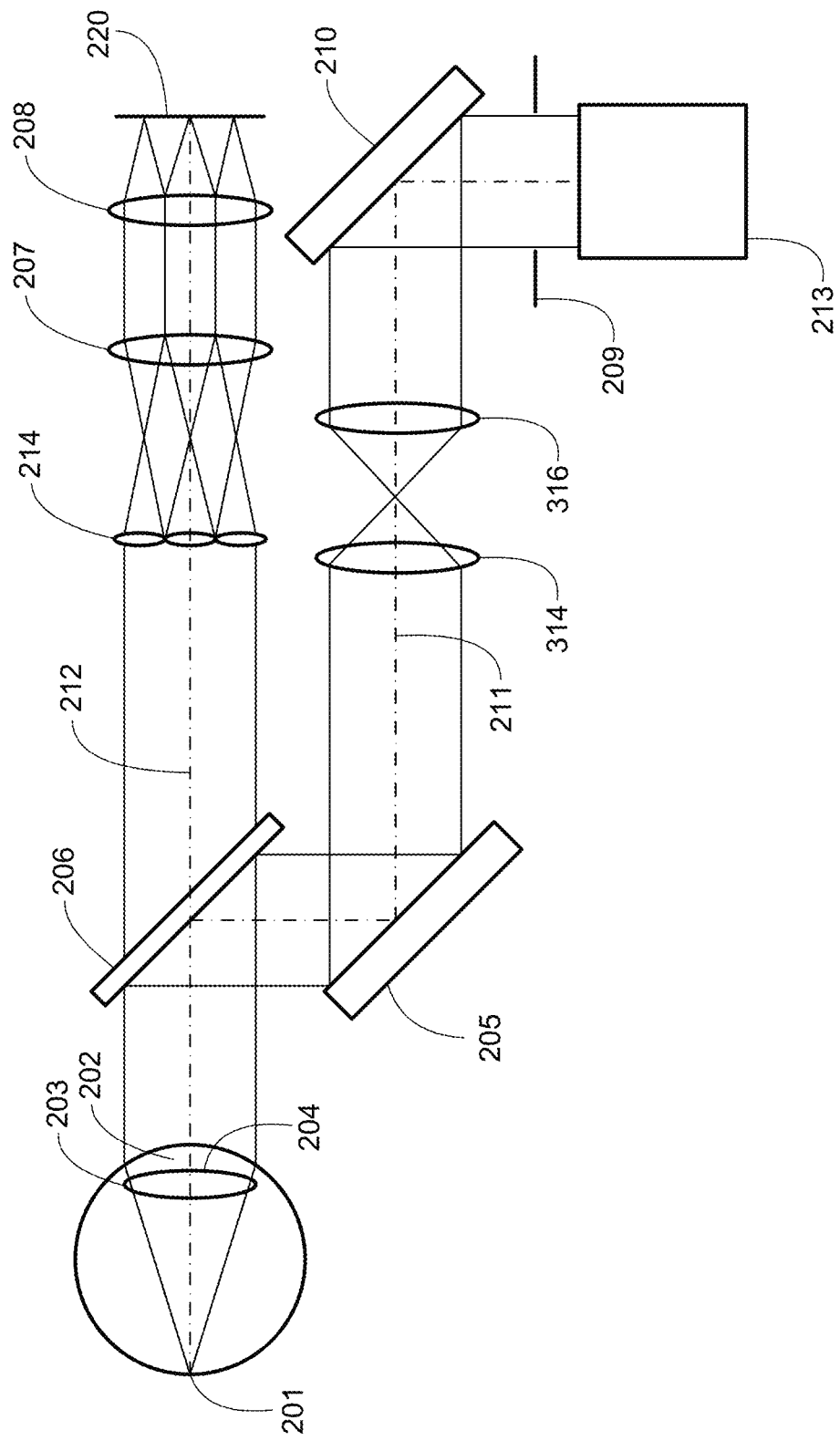
FIG. 3 illustrates an alternative design of the disclosed wavefront aberrometer.

FIGS. 2 and 3 are schematics of the optical components within the module and show the path of the light from its initiation to it being received on a two-dimensional light detector (220), such as the light detector (105) of FIG. 1.

In certain implementations, the module's light source (213), such as a laser, briefly turns on. In certain implementations, the light may pass through an aperture stop (209) to reduce the radius of the light beam. The light path is directed by reflectors (210, 205), and may be optionally focused as needed by passing through lenses (314, 316), as depicted in FIG. 3. In certain implementations, one or more of reflectors (205, 210) may be omitted and the light source (213) may be placed in a suitable location to direct the light beam toward the beam splitter (206).

The light source (213) may be of a sufficiently low power that prolonged exposure will not damage the patient's eye. This would allow for a user to turn on the light source (213) at the onset of the measurement and leave it on while one or more measurements are taken. Alternatively, the module may include a switch that would toggle power to the light source (213) in response to a signal sent from the mobile device, such as a Bluetooth or similar type signal, or that may be triggered by the firing of the mobile device's flash. In certain implementations, a shutter may be utilized to block light from the light source (213) until a measurement is to be taken. Power to the light source (213) may be supplied by a battery reversibly connected to the module, or the power may be drawn from the mobile device.

The light beam from the light source (213) is directed to the patient's eye by first directing the light beam along a first light path using a reflector (210), and then directing the light beam to a beam splitter (206) by reflector (205). The optional lenses (314, 316), reflectors (205, 210), aperture stop (209), beam splitter (206), and light source (213) may be referred to collectively as "optical components" or "a first plurality of optical components," which define a first light path (211) for the light beam to travel from the light source (213) to the patient's retina (201). The plurality of optical components are not limited to those shown, as additional lenses, beam splitters, reflectors, and apertures may be included as desired.

The reflection and transmission ratio of the beam splitter (206) may be selected to allow a sufficient amount of light to be delivered to the eye. The techniques used to determine the sufficiency of the light delivered to the eye and of altering the amount of light by changing the reflection and transmission ratio of the beam splitter are known in the relevant arts.

After the beam splitter (206), the collimated light is directed at the patient's eye where it enters the pupil (204) and is focused onto the retina (201) by the cornea (202) and the crystalline lens (203). The collimated light is reflected off the retina (201) and passes again through the crystalline lens (203) and cornea (202) as it exits the pupil (204). Thus, post-retinal light passes through the beam splitter (206) along a light path (212) and then through a microlens array (214), such as the microlens array (104) of FIG. 1. The microlens array (214) includes a plurality of lenses that split and transform the light into a two-dimensional array of individually focused spots (a "spot array") at the focal plane of the microlens array (214). The resulting spot array then passes through lens (207) and lens (208). These lenses (207, 208) create a conjugate image plane of the spot array onto the light detector (220). In certain implementations, the light detector is either a complementary metal-oxide-semiconductor (CMOS) or a charge-coupled device (CCD). In certain implementations, the lens (208) and the light detector (220) are components of the mobile device. The lens (208) may be the associated mobile device's camera lens, and may be also include of a series of lenses.

The lenses (207, 208), microlens array (214), and beam splitter (206) may also be referred to collectively as "optical components" or "a second plurality of optical components," which define a second light path for the light beam to travel from the patient's retina the light detector (220). It should be appreciated by one of ordinary skill in the art that at least a portion of the first and second light paths are coextensive. The term "coextensive" means that at least two defined volumes may occupy the same space. For example, two paths are said to be coextensive the paths are substantially parallel and overlapping.

Although the precision of the aberrometer increases as the number of lenses that are within the microlens array increases, increasing the number of lenses may decreases the dynamic range (the amplitude of the optical aberration) of the device. A lower dynamic range may prevent the aberrometer from measuring large aberrations. The number of aberrometer lenses may be further limited by the size of each microlens and the size of the light beam entering the microlens array. In certain implementations, the diameter of the light beam that enters the microlens array (214) is between about 2 and about 5 millimeters, corresponding to the size of the patient's undilated pupil (202), and the microlens array (214) may include between 5 and 25 lenses along the X-axis, and between 5 and 25 lenses along the Y-axis. In certain implementations, the number of lenses along the X-axis of the array is the same as the number of lenses along the Y-axis.

An alternative design of the optical components within the module is shown in FIG. 3. FIG. 3 differs from FIG. 2 by the inclusion of optional lenses (314, 316). Many of the implementations of the module do not include these components, in part, to reduce manufacturing costs, and in part to minimize the size of the module.

The optical designs of FIGS. 2 and 3 place the microlens array (214) within several tens of millimeters of the pupil (204), placing the distance within the Rayleigh range used in near field propagation, thereby providing a reasonable measurement of aberration even if the microlens array is not in the conjugate plane of the pupil. Such is described in Bauman, B. J., & Eisenbies, S. K. (2006), "Adaptive Optics System Assembly and Integration," in Porter, J., et al (Ed.), *Adaptive Optics for Vision Science: Principles, Practices, Design, and Applications*, Wiley-Interscience, pp 155-187, the disclosure of which is hereby incorporated by reference herein in its entirety.

Figure 4:
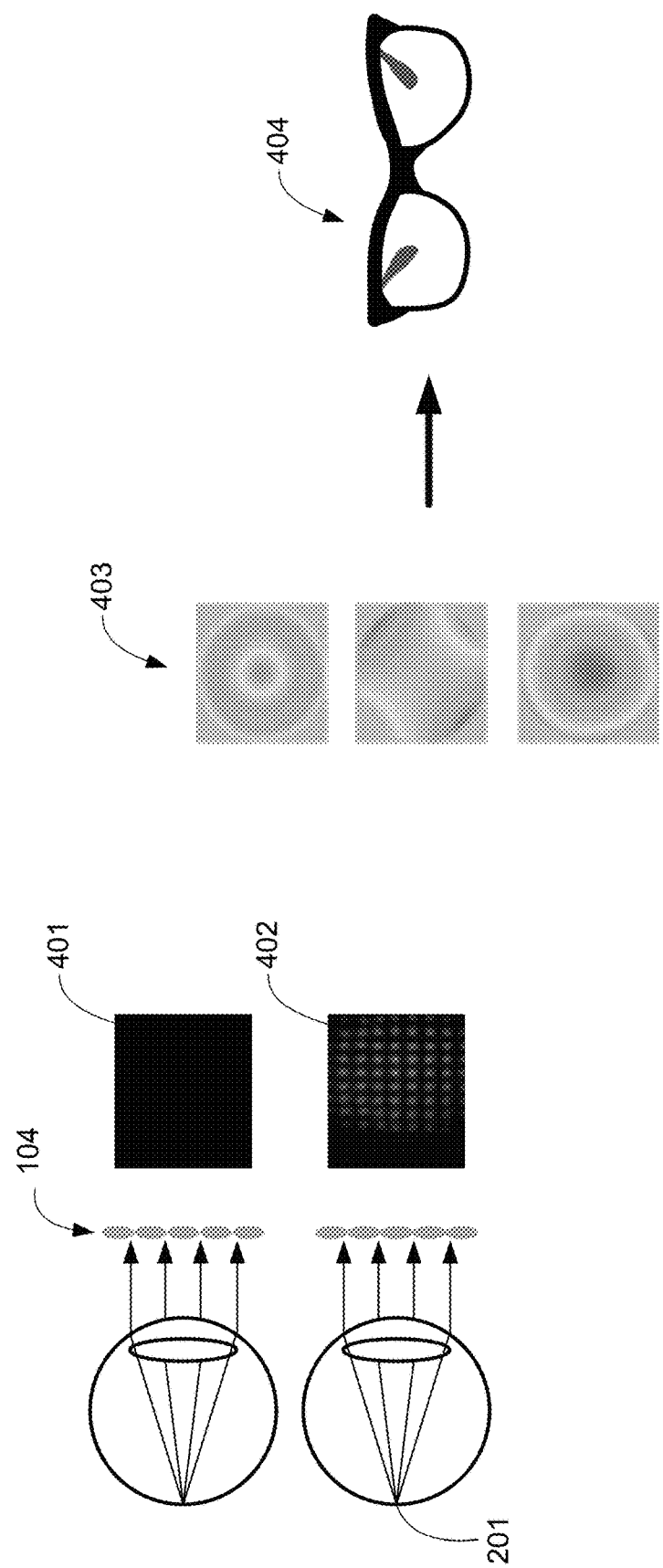
FIG. 4 depicts differences in Shack-Hartmann spots corresponding to a normal eye and an eye with refractive errors, and wavefront contour shapes representing defocus and astigmatism.

FIG. 4 illustrates how light reflected from a patient's retina may be captured by the mobile device's camera and examples of contour maps resulting from a transformation of the data. As described, light reflected from the retina is transformed into a spot array (401, 402) as it passes though the microlens array (410), such as any of the microlens arrays described herein. If the eye is free of aberrations (e.g., the left eye (411)), the resulting spot array captured by the mobile device's camera may be composed of evenly distributed spots (401). If instead the eye has aberrations (e.g., the right eye (412)), the resulting captured spot array may have distorted spot distribution (402).

The image of the spot array can be mathematically transformed though the use of algorithms known in the art by the computer on the mobile device itself, or by a computer capable of obtaining the image from the mobile device (collectively, the "computer"). One such transformation can be to create contour maps representing the aberrations of the eye (403). The spot arrays may also be transformed by a computer into an eye prescription that can be used to create corrective lenses (404) for the patient.

Although the primary source of light reflected off the patient's eye is of light reflected off the retina, a secondary source of the reflected light is that which may be reflected off the patient's cornea or crystalline lens. This corneal or lenticular reflective light ("noise") may be subtracted during processing by the computer or may otherwise be minimized through the use of methods and techniques known in the relevant art.

Figure 5:
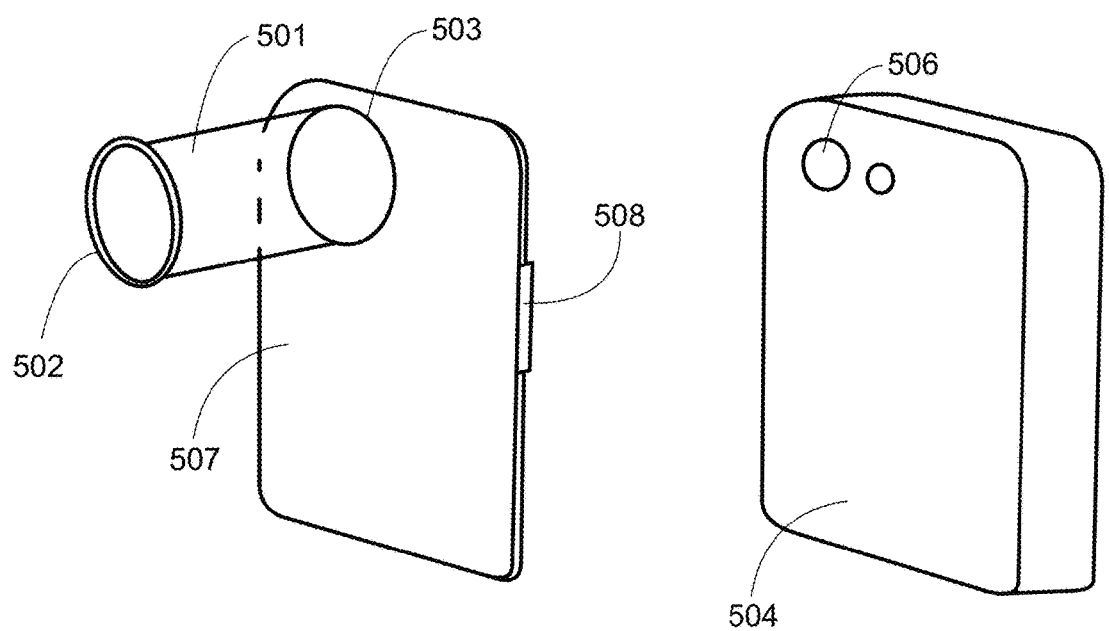
FIG. 5 is an illustration of an implementation of the module and an associated mobile device.

FIG. 5 is an illustration of an implementation of the module and an associated mobile device. In certain implementations, the optical components of the module are contained within a housing (i.e. a "light shaft"). In certain implementations, the light shaft may be tubular (i.e., a "light tube"), such as the light shaft (501) depicted in FIG. 5. The light shaft (501) includes an eye cup on one end (the "patient end" or "proximal end") (502), and at least one opening on the other end (the "device end" or "distal end") (503). The device end abuts and reversibly connects to the mobile device (504) by a connector. In certain implementations, the connector includes a back plate (507) that has at least one guide component (508). For example, the guide component (508) may be located along the perimeter of back plate (507). In certain implementations, at least two or three guide components may be included. In use, guide components reversibly attach to the mobile device so that the mobile device's light detector or camera (506) is aligned with the optical components contained within the light shaft (501) to receive light reflected from the patient's retina, also as described.

In certain implementations, a laser light source of the module is also contained within the light shaft (501), although alternative designs may have the laser outside of the light shaft (501). For example, the laser light source may be adjacent the light shaft (501), and accompanying optical components may direct light from the laser light source into the light shaft (501). In addition, the light shaft (501) may also include a user-accessible battery compartment that can hold the laser's power source. In certain implementations, the module's light source may be powered by the mobile device, and may receive a signal (either by a direct physical connection to the mobile device or a wireless receiver) from the mobile device to produce light. In certain implementations, the light source is removably attached to a receiving port of the module.

In certain implementations, the light shaft (501) may be a contiguous extension of the back plate (507) that extends proximally from a proximal surface of the back plate (507). The device end (503) of the light shaft (501) may define an opening through the back plate (507) such that light reflected from the patient's eye can pass through. In certain implementations, a distal surface of the back plate (507) may abut at least a portion of a surface of the mobile device (504) when the distal end of the light shaft (501) is positioned adjacent to the light detector of the mobile device (504).

Figure 6A:
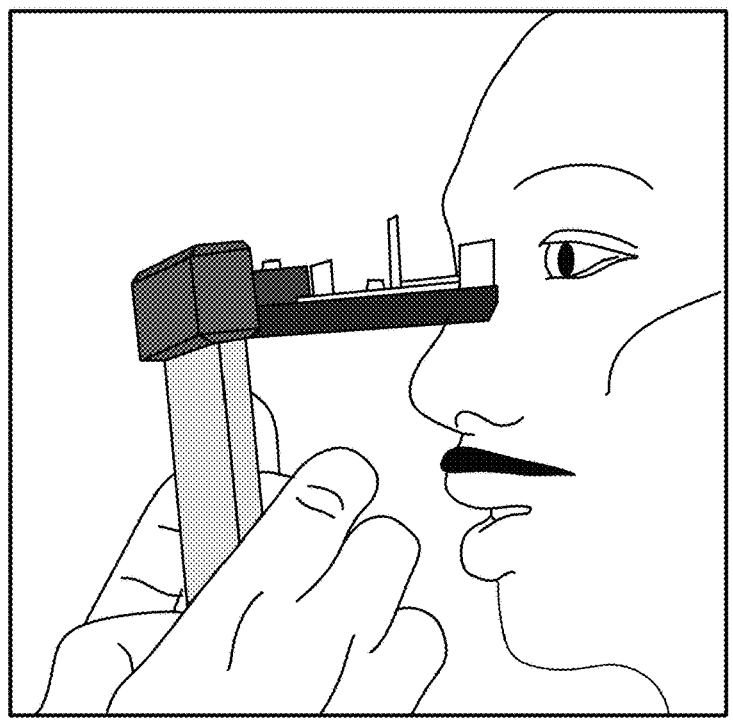
FIGS. 6A and 6B depict an illustrative module in use according to an implementation.
Figure 6B:
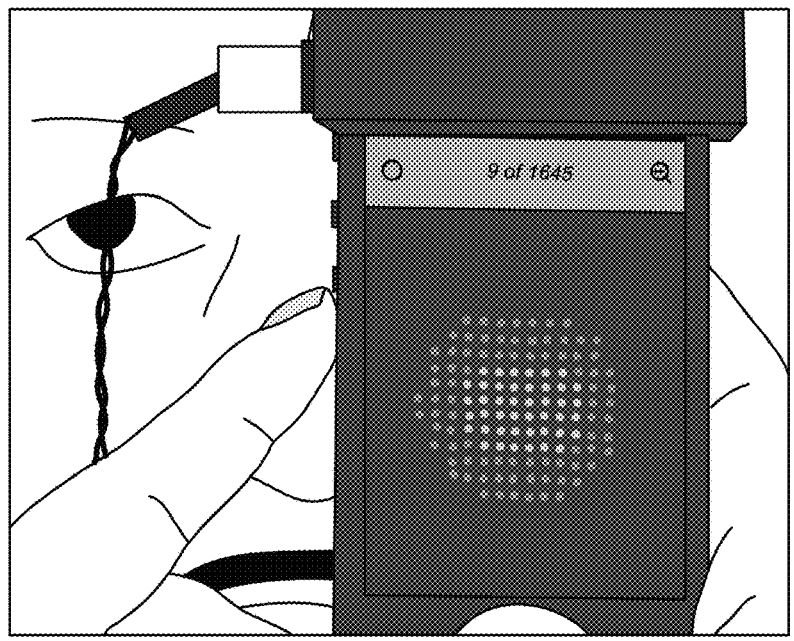

In certain implementations, the guide component (508) may allow the back plate (507) to snap to the mobile device. In certain implementations, the back plate (507) may include two guide components (508) disposed on opposite sides that allow the back plate (507) to slide onto the mobile device (504). In such implementations, a third guide component may be located at a top or bottom edge of the back plate (507) that prevent further sliding in order to position the light shaft (501) to be adjacent to the light detector (506) of the mobile device (504). In certain implementations, the back plate (507) may be omitted entirely. For example, a portion of the light shaft (501) may snap directly onto the mobile device (504). In certain implementations, the guide component (508) may be a slot that is wide enough to receive and retain a portion of the mobile device (504), e.g., as illustrated in FIGS. 6A and 6B. In certain implementations, the connector that positions the light shaft (501) may be an adhesive material that causes the light shaft (501) to stick to the mobile device (504). In such implementations, the adhesive material may be disposed on the distal surface of the back plate (507). In certain implementations, the connector may include multiple pieces that extend from the distal end of the light shaft (501) and are configured to engage and/or wrap around the mobile device (504). In certain implementations, the connector may include alignment marks that indicate how to position the light shaft (501) with respect to the light detector (506).

It is to be understood that the tubular shape of the light shaft (501) is merely an illustrative example of a light shaft, and any structure that arranges the optical components of the module, such as an enclosed housing, a partially enclosed housing (e.g., as depicted in FIG. 6A), a plate, or any suitable combination thereof, may be considered to be a light shaft.

The exact conformation and size of the optical components housed within the light shaft (501) can be determined through the use of equations and techniques known in the art. In certain implementations, the positioning of the optical components and the opening at the device end of the light shaft (501) is fixed in position during manufacturing so that the opening corresponds to the position of the mobile device's camera lens such that the outgoing, or reflected, light path is aligned to the mobile device's camera lens.

In use, the device end of the light shaft (501) may be reversibly connected to the mobile device, and the patient end of the light shaft (501) is held against the patient's eye socket. When the module's light source is actuated, the light from the light source travels to the patient's retina as disclosed, and this light is reflected to the mobile device's camera, also in the disclosed manner. The data captured by the light detector or camera is either processed by the mobile device (e.g., by an application running on the mobile device), or transmitted to another computer for processing. In this manner, the patient may, if the implementation of the software allows, monitor their own refraction or Snellen fraction. Other implementations of the software may transfer the data to a medical provider for diagnostic or monitoring purposes, or may transfer the data to a corrective lens provider for the purpose of providing corrective lenses to the patient. A wavefront aberrometer module as described in this application thereby allows a patient to obtain measurements of retinal aberrations without having to travel to an office of ophthalmology or optometry, likely increasing compliance with recommended refraction measurements.

Figure 7:
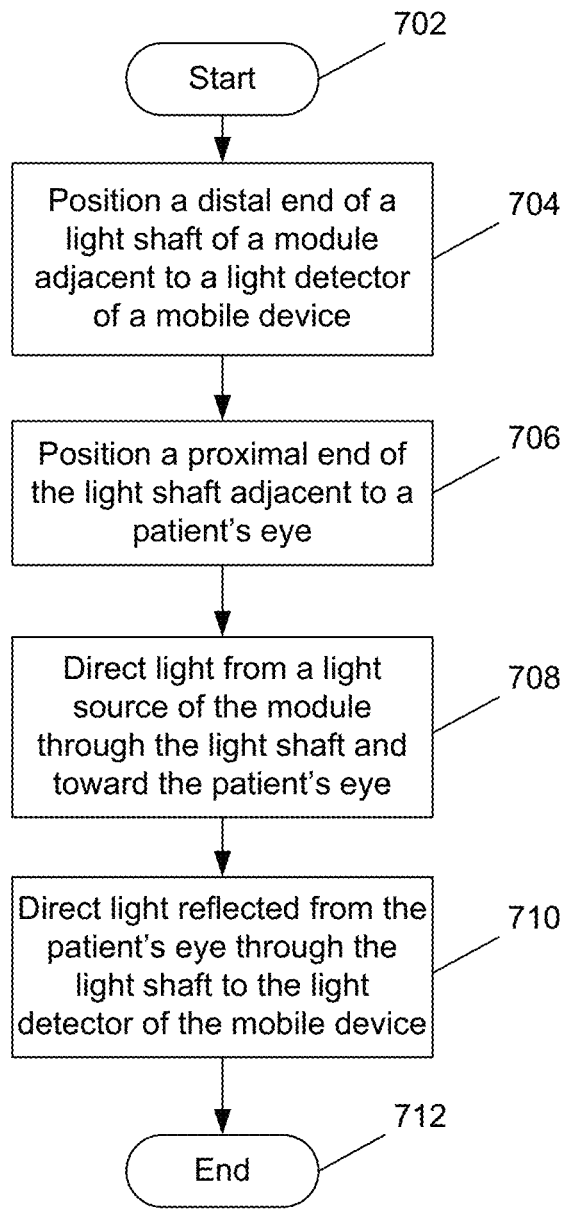
FIG. 7 is an illustrative process for measuring an aberration of a patient's eye using any of the implementations disclosed herein.

FIG. 7 is an illustrative process for measuring an aberration of a patient's eye using any of the implementations disclosed herein. The process (700) begins at step (702). At step (704), a distal end of a light shaft of a module is positioned adjacent to a light detector of a mobile device. The light shaft may correspond to any implementation disclosed herein, such as the light shaft (501) of FIG. 5 or the light shaft of FIG. 6A. The mobile device may be any type of mobile device described herein, such as the mobile device (504) of FIG. 5. In certain implementations, the light shaft may be placed adjacent to the light detector of the mobile device by removably attaching the light shaft to the mobile device by a connector, such as back plate (507) and guide component (508) of FIG. 5.

At step (706), a proximal end of the light shaft is positioned adjacent to a patient's eye. For example, the proximal end may abut the patients eye or be placed a distance away so as to not physically contact the patient. The proximal end may similar to the end (502) and may have an eye cup.

At step (708), light is directed from a light source of the module through the light shaft and towards the patient's eye. This may be accomplished, for example, using a first plurality of optical components, such as the optional lenses (314, 316), aperture stop (209), reflectors (205, 210), and beam splitter (206) of FIGS. 2 and 3.

At step (710), light reflected from the patient's eye is directed through the light shaft to the light detector of the mobile device. This may be accomplished, for example, using a second plurality of optical components, such as the lenses (207, 208, 214, 314, 316), pinhole aperture (315), and beam splitter (206) of FIG. 3.

In certain implementations, the data generated in response to directing the light reflected from the patient's eye to the light detector may be processed, for example, by the mobile device itself (using a processor of the mobile device) or a separate device. The data processing may include measuring a retinal aberration of the patient, in accordance with the methods described herein. In the implementations in which a separate device processes the data, the mobile device may be configured to transmit the data (either processed or unprocessed) to the separate device.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A portable wavefront aberrometer comprising:
a housing having a proximal end and a distal end, wherein an aperture is formed in the housing at the proximal end;
an activatable light source;
a light detector; and
optical components housed within the housing, the optical components comprising a microlens array, a plurality of lenses, one or more reflectors, and one or more beam splitters, wherein the optical components are arranged to define a first light path and a second light path such that:
light generated by the light source, when activated, is directed, by a first subset of the optical components, along the first light path through the aperture at the proximal end of the housing,
light received into the housing through the aperture at the proximal end of the housing is directed, by a second subset of the optical components, along the second light path to the light detector, and
a two-dimensional spot array is formed on the light detector as a result of the light received into the housing passing through the microlens array prior to reaching the light detector.

2. The portable wavefront aberrometer of claim 1, wherein the microlens array comprises a plurality of microlenses arranged in in a two-dimensional array, wherein a total number of microlenses of the microlens array ranges from 25 to 625.

3. The portable wavefront aberrometer of claim 2, wherein the light source comprises a laser.

4. The portable wavefront aberrometer of claim 3, wherein the portable wavefront aberrometer is configured to compute a patient-specific parameter from an image of the two-dimensional spot array captured by the light detector, wherein the patient-specific parameter comprises a Snellen fraction, a measurement of an optical aberration, or an eyeglasses prescription.

5. The portable wavefront aberrometer of claim 3, wherein the portable wavefront aberrometer is configured to transmit an image of the two-dimensional spot array captured by the light detector to a computing device of a medical provider.

6. The portable wavefront aberrometer of claim 5, wherein the computing device is to compute a patient-specific parameter from the image, wherein the patient-specific parameter comprises a Snellen fraction, a measurement of an optical aberration, or an eyeglasses prescription.

7. The portable wavefront aberrometer of claim 1, wherein the portable wavefront aberrometer is assembled by coupling a mobile device to the housing at the distal end of the housing, and wherein the light detector is integrally formed in the mobile device.

8. The portable wavefront aberrometer of claim 7, wherein the housing comprises a connector located at the distal end of the housing, the connector comprising at least one guide component for positioning the mobile device such that the second light path terminates at the light detector.

9. The portable wavefront aberrometer of claim 8, wherein the at least one guide component is a slot for receiving the mobile device.

\* \* \* \* \*